(12) United States Patent
Jin et al.

(10) Patent No.: US 10,197,491 B2
(45) Date of Patent: Feb. 5, 2019

(54) METHOD FOR POROSITY MEASUREMENT USING SEM IMAGES OF ROCK SAMPLES REACTED WITH A GADOLINIUM COMPOUND

(71) Applicant: Korea Institute of Geoscience and Mineral Resources, Daejeon (KR)

(72) Inventors: Jae Hwa Jin, Daejeon (KR); Young Min Oh, Daejeon (KR); Jun Ho Kim, Daejeon (KR); Jeong-Yil Lee, Daejeon (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 0 days.

(21) Appl. No.: 15/799,705

(22) Filed: Oct. 31, 2017

(65) Prior Publication Data

US 2018/0120215 A1 May 3, 2018

(30) Foreign Application Priority Data

Nov. 1, 2016 (KR) ........................ 10-2016-0144303

(51) Int. Cl.
*G01N 15/08* (2006.01)
*H01J 37/26* (2006.01)

(52) U.S. Cl.
CPC ........... *G01N 15/088* (2013.01); *G01N 15/08* (2013.01); *H01J 37/26* (2013.01)

(58) Field of Classification Search
None
See application file for complete search history.

(56) References Cited

U.S. PATENT DOCUMENTS 4,628,468 A * 12/1986 Thompson ........... G01N 15/088
356/445
4,982,086 A * 1/1991 Withjack ............. G01N 15/088
250/255

(Continued)

FOREIGN PATENT DOCUMENTS

| CN | 102294038 B | * | 2/2013 | ............. G01N 15/08 |
| WO | WO-2013039416 A1 | * | 3/2013 | ........... G01N 15/088 |
| WO | WO-2017129812 A1 | * | 8/2017 | ............. G01N 15/08 |

OTHER PUBLICATIONS

Jae Hwa Jin et al., "Correlative multiple porosimetries for reservoir sandstones with adoption of a new reference-sample-guided computed-tomographic method", Scientific Reports, Jul. 22, 2016, vol. 6, Article 30250, Macmillan Publishers Limited.

*Primary Examiner* — Michael J Logie
(74) *Attorney, Agent, or Firm* — Hauptman Ham, LLP

(57) ABSTRACT

The present invention relates to a method for measuring porosity of a rock according to the present invention including: (a) capturing a first image by using SEM with respect to a rock sample; (b) determining a first area of a portion determined to be a heavy mineral in the first image; (c) immersing the rock sample in an aqueous solution in which a gadolinium compound is dissolved in that the aqueous solution flows into pores and the gadolinium compound is deposited in pores inside the rock sample; (d) capturing a second image by using SEM with respect to the rock sample; and (e) determining a second area of a portion determined as a heavy mineral and a pore in the second image, and then subtracting the first area from the second area to determine an area of pores in the rock sample.

11 Claims, 7 Drawing Sheets

(56) References Cited

U.S. PATENT DOCUMENTS

| | | | | |
|---|---|---|---|---|
| 4,983,376 | A  * | 1/1991 | Sherry | A61K 49/06 |
| | | | | 424/9.363 |
| 2010/0128933 | A1* | 5/2010 | Derzhi | E21B 49/005 |
| | | | | 382/109 |
| 2011/0272325 | A1* | 11/2011 | Soane | C09K 8/524 |
| | | | | 208/14 |
| 2011/0306525 | A1* | 12/2011 | Lighthelm | C09K 8/58 |
| | | | | 507/225 |
| 2012/0197526 | A1* | 8/2012 | Leyte Guerrero | G01N 15/088 |
| | | | | 702/2 |
| 2013/0259190 | A1* | 10/2013 | Walls | G01N 23/22 |
| | | | | 378/9 |
| 2014/0183357 | A1* | 7/2014 | Smith | G01N 23/2252 |
| | | | | 250/307 |
| 2015/0122992 | A1* | 5/2015 | Owen | G01N 23/225 |
| | | | | 250/307 |
| 2017/0017011 | A1* | 1/2017 | Howard | G01N 15/088 |
| 2017/0115200 | A1* | 4/2017 | Chen | G01N 15/082 |
| 2018/0003786 | A1* | 1/2018 | Washburn | G01R 33/44 |

* cited by examiner

High Brightness Area (white/light colored) = 2.85%

High Brightness Area (white/light colored) = 1.11%

High Brightness Area (white/light colored) = 7.34%

Low Brightness Area (black/dark colored) = 1.45%

Sum of High and Low Brightness Area = 8.79%

High Brightness Area (white/light colored) = 7.34%

METHOD FOR POROSITY MEASUREMENT USING SEM IMAGES OF ROCK SAMPLES REACTED WITH A GADOLINIUM COMPOUND

CROSS REFERENCE TO RELATED APPLICATION

This application claims priority to and the benefit of Korean Patent Application No. 10-2016-0144303 filed in the Korean Intellectual Property Office on Nov. 1, 2016, the entire contents of which are incorporated herein by reference.

BACKGROUND OF THE INVENTION

The present invention relates to a technique in the geological and resource fields for measuring porosity of a rock which forms a stratum, and more particularly, to a method for measuring porosity of a rock by using an SEM image.

To qualitatively and quantitatively determine the distribution of pores in a rock is a very important technique. For example, when the porosity in an oil gas-storage reservoir is measured, an amount of oil and gas resources may be calculated, and when information about porosity is used to calculate a transmittance, how much and how the oil and gas resources may be recovered may also be determined.

Accordingly, regarding techniques for measuring porosity of rocks forming a stratum, a variety of methods have been developed, existing methods may be continuously improved by succeeding research, or novel methods may also be developed.

In particular, since resources in traditional reservoirs such as sandstone are exhausted, resource extraction is performed in a non-traditional reservoir such as dense strata or shale, which has very small pores and a much more complicated pore structure. Accordingly, the demand for a technique of more efficiently and accurately measuring a fine-scale porosity in such rocks has come to the fore.

Meanwhile, the present inventors published a paper in which pros and cons of all sorts of techniques widely used for analyzing pores in rocks, and the description herein will be provided with reference to the corresponding paper.
Related paper: Jae Hwa Jin, Junho Kim, Jeong-Yil Lee, and Young Min Oh, 2016, Correlative multiple porosimetries for reservoir sandstones with adoption of a new reference-sample-guided computed-tomographic method, Scientific Report 6 (30250): 1-10.

Referring to the related paper, techniques of analyzing pores in a rock which have been used since the development thereof may be classified into three categories, for example: 1) a technique of extracting all substances distributed in the pores in a rock, that is, pore-filling substances such as oil and water and measuring the amount thereof, thereby additionally securing pore information; 2) a technique of forcibly inserting fluid substances in the pores and measuring porosity on the basis of the inserted amount; and 3) a technique of imaging the rock using an electronic apparatus, and then separating and identifying the pores from a medium by using a graylevel difference on the image of the medium and the pores from the captured image and thereby embodying a pore structure and measuring porosity of the pore structure; and the like.

As introduced in the related paper, the techniques of example 1) among the above-mentioned pore analyzing techniques include a Dean-Stark method, a retort method, and the like, the techniques of example 2) include a mercury intrusion porosimetry, a helium gas intrusion method, a gas adsorption method, and a ultra-pure water immersion method, and the like, and the techniques of example 3) which are more actively being studied recently include a method of imaging the medium and pores of a rock to be analyzed by using an electronic apparatus such as X-ray computed tomography (CT) or scanning electron microscopy (SEM), and then quantitatively calculating the characteristic values of the pores.

However, each of the above-mentioned pore measuring methods has a measuring limit. For example, in the case of a method such as that of example 1), substances filling the pores should be, of course, conserved as it is before a pore measuring experiment, samples need to be pulverized to extract the corresponding substances completely, and information about a pore structure is therefore difficult to obtain. In the case of example 2), a measuring limit is determined for each kind of injected substance for pore measurement. That is, in the case of the mercury intrusion porosimetry, a pore having a very small size of nanometer level is difficult to measure, and conversely, in the gas adsorption method, a large pore having a size level of micrometer or greater is difficult to measure. In addition, when a gas is used as in the helium gas intrusion method or the gas adsorption method, since a bulk volume data need to be borrowed from other methods, the method is difficult to be a completely independent measurement, and in the case of the ultra-pure water, the accuracy of the pore measurement is unsatisfactory.

Meanwhile, in the case of example 3), there is a merit in that not only a qualitative measurement of the pores but also the information about a pore structure may be obtained together because the medium and pores of a given sample are imaged as it is, but conversely, has a limitation in that pores having nanometer-level sizes are difficult to measure due to a resolution limit in the current technical level of CT technology.

When an SEM is used, a two-dimensional pore structure is obtained by processing the sample into a thin-section sample and observing the surface of the sample. Meanwhile, since a specific portion of the sample may be imaged to be magnified up to several thousands of thousand times, in particular, rocks of non-conventional reservoir in which pores having nanometer-level sizes occupy majority may be helpfully measured. The technique using an SEM may be the best in terms of accuracy. However, in the conventional SEM image analysis method, when pores and other rock media inside a rock to be analyzed are not clearly identified on an SEM image, the pore measurement becomes inaccurate. The reason for this is because media of the whole or a portion of the rock to be analyzed are formed of substances having electron densities not so higher than those of the pores and thereby does not show a clear graylevel difference on an SEM image compared to the pores. A representative example is the case in which the whole or a portion of the media in a rock is formed of low-density substances such as porous clay mineral aggregates or solid kerosene. Pores present in association with such substances have graylevels that are not so different from the surrounding medium substances, have sizes that are also very small in such a degree to reach a micrometer or nanometer level, and thus, have limitations of not being easily identified even on an SEM image.

SUMMARY OF THE INVENTION

An aspect of the present invention provides a method for measuring porosity of a rock, the method having an improved accuracy and measuring the porosity of a rock through an SEM image analysis, wherein not only a fine porosity of even a nano scale in the rock may be identified, but also pores and heavy minerals in the rock may be clearly distinguished.

According to an aspect of the present invention, there is provided a method for measuring porosity of a rock including: (a) capturing a first image with respect to a rock sample the porosity of which is to be measured by Scanning Electron Microscope; (b) determining a first area of a portion determined as heavy minerals in the first image; (c) immersing the rock sample in an aqueous solution in which a gadolinium compound is dissolved in that the aqueous solution flows into pores and the gadolinium compound is deposited in pores inside the rock sample; (d) capturing a second image after the gadolinium compound is deposited by performing an Scanning Electron Microscope with respect to the rock sample; and (e) determining a second area of portions determined as heavy minerals and pores, and then subtracting the first area from the second image to determine an area of pores of the rock sample.

According to the present invention, the first area and the second area may be determined by graylevels on an image.

In addition, the gadolinium compound used may be, for example, gadolinium nitrate ($GdN_3O_9 \cdot 5(H_2O)$).

In an embodiment of the present invention, before the first image and the second image are captured, a preprocessing including grounding of a surface of the rock sample may be preferably performed, and aside from grinding, the preprocessing may favorably include coating the surface of the rock sample with a material including gold or platinum having a high electrical conductivity.

Meanwhile, in an embodiment of the present invention, the concentration of the gadolinium compound may favorably be formed thick in proportion to sizes of pores of the rock sample.

In an embodiment of the present invention, when the rock sample is immersed in the aqueous solution of gadolinium compound, the gadolinium aqueous solution may be heated directly or by using an oven so as to improve a penetration rate of the gadolinium aqueous solution into the rock sample. Alternatively, air and water components may be favorably discharged from the pores of the rock sample by performing heating in a vacuum chamber. Vacuum processing and heating may be separately performed, or sequentially performed, or a selected combination thereof may be performed.

In an embodiment of the present invention, the step of immersing the rock sample in an aqueous solution of the gadolinium compound may be favorably performed until the gadolinium compound is deposited in the aqueous solution of the gadolinium compound.

DETAILED DESCRIPTION OF PREFERRED EMBODIMENTS

Figure 1:
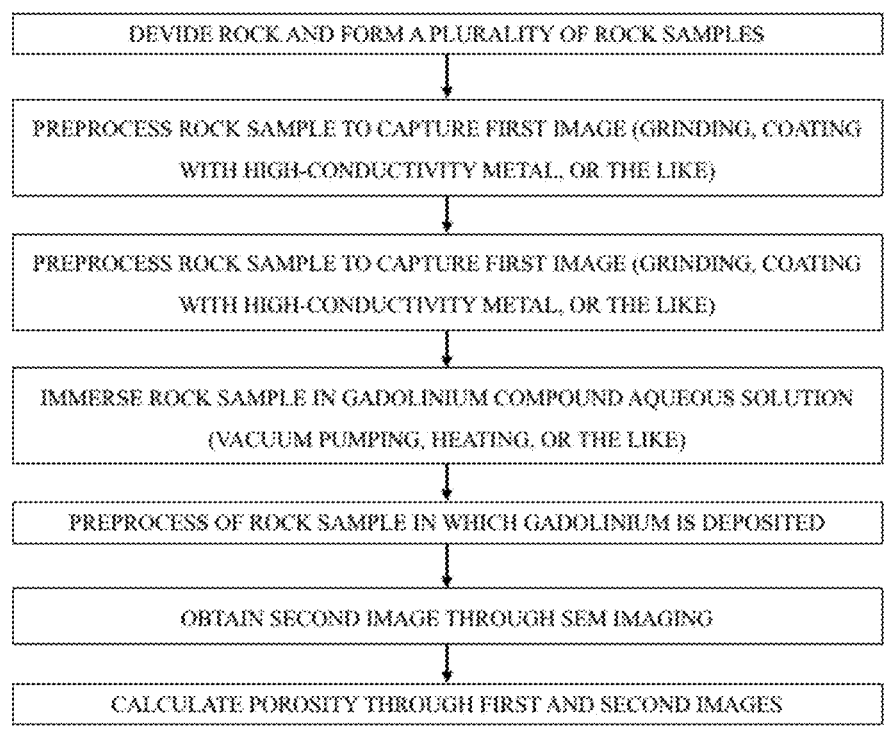
FIG. 1 is a schematic flowchart of a method for measuring porosity of a rock according to an embodiment of the present invention.

First, the terms or words used in this specification should not be interpreted as limited to a commonly used meaning or a meaning defined in dictionaries, and should be interpreted as having a meaning that is consistent with their meaning in the context of the technical idea of the invention, based on the principle that an inventor may properly define the meaning of the words or terms to best explain the invention.

In addition, in this specification, the expression of porosity may be interpreted according to "porosity from core analysis" (core analysis porosity) in an academic sense. In addition, the "porosity from core analysis" (core analysis porosity) is defined to be divided into a "porosity from analysis of oven-dried cores (oven-dried core analysis porosity) and a "porosity from analysis of humidity-dried cores (humidity-dried core analysis porosity). These are the cases varying according to whether a sample is dried prior to the measurement of porosity, and also in the present invention, terms representing a drying method may be additionally expressed according to what method described in the above is selected and used from among the sample drying methods.

First, a fundamental theory of the present invention will be described.

In the present invention, a method of analyzing an SEM image obtained by SEM imaging is used for measuring porosity of a rock sample. As also described in the related arts, the method of using an SEM image had a limitation in that in a rock formed of low-density substances such as clay minerals or solid kerosene, pores and rock media were not clearly separated in the image. Basically, SEM images use a principle that brightness (graylevel) in an image varies according to a difference in electron densities, and when media are formed to have a low density similar to pores, the media all appear dark on an SEM image.

Accordingly, in the present invention, in order that pores and rock media are clearly discriminated in an SEM image, a method of inserting a high-density metal into pores of a rock sample is adopted. In order to be inserted into fine pores, heavy metal should be formed into an aqueous solution. In the present invention, a variety of aqueous heavy metals may be adopted, but an aqueous solution which is prepared by dissolving a gadolinium compound in water is used.

That is, with respect to a rock sample, first, a first image is obtained by Scanning Electron Microscope, the rock sample is then immersed in the aqueous solution of a gadolinium compound to thereby allow the aqueous solution to penetrate into pores of the rock sample and allow the gadolinium compound to be deposited in the pores. After the gadolinium compound is deposited, a second image is captured again by the. The porosity of the rock sample may be measured from the first and second images.

As described above, in the present invention, the electron density in the pores are increased by using the gadolinium compound, and thus, rock media and pores are allowed to be separated in the SEM image. However, in this case, one limitation is the presence of heavy metals or heavy minerals contained in the rock sample. Heavy minerals have high electron densities and therefore appear bright also in the first image of the rock sample captured before the gadolinium compound penetrates thereinto. In addition, the gadolinium compound has a characteristic of being easily bonded with heavy metals. For example, gadolinium may be deposited onto the surfaces of heavy minerals through electrical bonding or the like. Accordingly, also in the second image captured after immersing the rock sample in the gadolinium compound, the heavy minerals appear bright as in the pores in which the gadolinium compound is deposited.

Accordingly, in the present invention, there was developed a method in which an area (a first area) of portions appearing bright in the first image captured before processing the gadolinium compound was subtracted from the total area (a second area) of the portions appearing bright in the second image captured by an electron microscope. Through this, only the area of pure pores may be separated except for heavy minerals in the rock sample, and thus, the porosity of the rock sample may be accurately measured.

Hereinafter, with reference to the accompanying drawings, a porosity measuring method (hereinafter, referred to as a "rock porosity measuring method") by using an Scanning Electron Microscope image of a rock sample, reacted with a gadolinium compound according to an embodiment of the present invention, will be described in detail.

FIG. 1 is a schematic flowchart of a method for measuring porosity of a rock according to an embodiment of the present invention.

Referring to FIG. 1, in the method for measuring the porosity of a rock, a rock sample is first secured. The rock sample to be measured may be highly diversified. For example, when a reservoir of an oil field or shale gas field is to be evaluated, a core sample may be secured through test drilling. Alternatively, to evaluate a throughput of an underwater aquifer, geological strata forming an aquifer may be cored. In addition, in the present invention, aside from the core sample, various rock samples may be used to perform a scientific research in the geological field. That is, in the present invention, samples the pores of which are to be measured may be diversified not only over the fields of resource and geology, but also over the fields of a general industry and academy.

At this point, the rock sample is processed into a sample form from rocks obtained by coring or excavation, and the rock sample used to capture a first image may be used as it is to capture a second image. Alternatively, the rock sample used to capture the first image may be different from that used to capture the second image after a gadolinium compound is deposited. But, also in the case of using different rock samples, the two samples, each of which is separated and processed from the same rock, are used. Logically, the rock samples used to capture the first and second images should be the same, but samples different from each other may be used without a problem as long as the samples have been separated from the same rock. That is, the two rock samples are not completely the same, but there is no significant difference in porosities or heavy mineral contents. In addition, when portions adjacent to each other in a rock are separated and used, the two samples will exhibit nearly the same property. That is, properties of rocks vary according to the cause of formation thereof or while undergoing weathering and metamorphic processes because a rock exhibits, as a whole, a uniform property. In particular, pores and contents of heavy minerals appear uniform over the entire rock with a few errors only. Conversely, measuring the porosity of a stratum by using a core sample cored from a rock means that the porosity of the rock forming the stratum is uniformly guaranteed by the core sample. However, when the rocks that form the stratum vary, such representability and the uniformity are not guaranteed. In the present invention, two samples are used, but the samples separated from one rock are used, and thus, it is estimated that there is no difference compared to a case in which the first and second images are captured from one sample. Rather, when the first and second images are captured, the phenomenon that the sample is distorted in a preprocessing process may be minimized by using separate samples. This will be additionally described after the preprocessing of the sample is described.

Further, in the present invention, since a method, in which porosity is measured by performing the same test with respect to several portions of a rock and an average value of porosity is obtained, is adopted, non-equality of rock samples will cause no problem.

The rock sample is processed in a shape of a thin section or a ground section. For example, precise surface finishing, such as argon beam milling, is performed on the surface of the rock. In addition, the ground surface of the rock sample may be coated with metals having high electrical conductivities such as gold and platinum, which is a method widely used for preprocessing of SEM imaging.

However, the preprocessings described above, that is, pulverization, flattening, shape processing, surface grinding, finishing, coating with metals having high electrical conductivities are selectively performed. All the preprocessings may not be performed, or all the above-mentioned preprocessings may also be performed. Alternatively, some processes from among the preprocessings may be performed. Such preprocessings are all for improving clarity and quality of the SEM image, and the contents of the preprocessings may vary according to the condition of the rock sample.

The above description in which using two samples is rather preferred than using one rock is provided because the above-mentioned preprocessings should be performed when the SEM image is captured. That is, since the second image cannot be captured in a state in which the preprocessing described above is performed on the surface of the rock to capture the first image, a new cross-section of the surface of the rock sample should be formed, and the preprocessing should be performed again. In any case, although one sample is used, the same cross-section cannot be imaged. Accordingly, the first image is captured by performing a preprocessing with respect to one sample, a new cross-section is formed again from the sample, and then a gadolinium compound processing and a preprocessing should be performed. When the first and second images are captured with respect to the same sample, the state of the sample distorted in the preprocessing process before the first image is captured may affect the capturing of the second image, and thus, the initial state of the sample may not rather be accurately reflected. Consequently, it is advantageous that from the first, the rock sample is divided into two samples and the first and second images are respectively captured by using two samples.

As described above, after the preprocessing with respect to the rock sample is completed, the first image is captured by using an electron microscope. Each of a plurality of portions may be imaged from a cross-section of the rock sample. When the plurality of portions are imaged, the image capturing conditions which are set in the hardware and software of the electron microscope are set to be the same maximally. For example, intensity of voltage and current, magnification, image size, image scan peed, brightness, contrast, detector type, vacuum or non-vacuum, and the like are favorably set to be the same.

When the first image is captured through SEM imaging, heavy minerals are sorted by using graylevels in the first image. Since the heavy minerals appear bright on the SEM image, the area (first area) of portions exhibiting brightness equal to or greater than a predetermined level in the entire area of the first image is separately calculated. The calculated result may be expressed as a percent ratio with respect to the entire area.

When the capture of the first image and the determination of the area of portions of the heavy minerals are completed, a process of depositing the gadolinium compound is then performed with respect to the rock sample. Gadolinium, which is a heavy metal, exhibits a water solubility of being easily dissolved into water. In the present invention, a variety of gadolinium compounds may be used, and in this embodiment, gadolinium nitrate is dissolved into water and is formed in an aqueous solution state. In addition, the rock sample is immersed in the gadolinium aqueous solution such that the gadolinium aqueous solution penetrates into pores in the rock sample.

The important point is to enhance a penetration rate. A method of enhancing the penetration rate will be proposed in this embodiment.

First, the concentration of the gadolinium compound is important. That is, when the concentration of the gadolinium compound is high, more amount of the gadolinium compound may be deposited in the pores. Therefore it is advantageous to discriminate pore portions in the SEM image. However, when the concentration is high, the penetration rate is unfavorably decreased. In particular, when the pores have fine sizes such as several to several tens of nanometers, an aqueous solution having a high concentration is difficult to penetrate into the pores. Accordingly, when the sizes of the pores are fine, the concentration of the aqueous solution may favorably be decreased to enhance the penetration rate. Conversely, when the sizes of the pores are large, the concentration of the aqueous solution is favorably increased.

In particular, when the concentration of the aqueous solution is high, the speed of deposition of the gadolinium compound is increased, and the test time may therefore be reduced.

In addition, the gadolinium compound may be deposited in the pores, but may also be deposited on the surface of heavy minerals in the rock sample due to an electrical action or the like. Also in this case, an aqueous solution having a high concentration is advantageous because the reaction time may be reduced.

A second method of enhancing the penetration rate is to use vacuum pumping. A rock sample is immersed in a container filled with an aqueous solution of the gadolinium compound, the entire container is received inside a vacuum chamber, and a vacuum pressure is applied. When the vacuum pressure is applied, air and water in the rock sample is discharged, and the aqueous of the gadolinium compound may penetrate more quickly and deeply into the empty pores.

Meanwhile, the aqueous solution of the gadolinium compound penetrates into the pores, and then, while the gadolinium compound is rapidly deposited, the phases of water and the compound may be separated. When the gadolinium compound is deposited in advance even before the aqueous solution of the gadolinium compound penetrates into the rock sample up to a deep portion, this may be unfavorable in terms of the penetration rate. Accordingly, it is favorable that the aqueous solution of the gadolinium compound, in which the rock sample is immersed, be heated, thereby, delaying the deposition time, and allowing the aqueous solution to penetrate into a deep pores of the rock sample. An oven or the like may be used for heating. The vacuum pumping and the heating may be performed together, or may also be selectively or repeatedly performed.

As described above, the aqueous solution of the gadolinium compound is allowed to penetrate into all the pores in the rock sample by using the concentration of the aqueous solution, vacuum pumping and heating. Then, how long the time sufficient for the penetration is set should be determined. In this embodiment, the rock sample is immersed in the aqueous solution of the gadolinium compound until a deposition occurs in the in the aqueous solution of the gadolinium compound filled in the container. That is, when the vacuum pumping is adopted, the gadolinium compound is deposited in the gadolinium compound aqueous solution having penetrated into pores in the rock sample, and the phase-separated water may be discharged as moisture by the vacuum pumping. The same phenomenon also occurs outside the rock sample. That is, when the vacuum pumping is continuously performed, while water components are pumped in a steam state also in the gadolinium compound aqueous solution outside the rock sample, the concentration of the gadolinium compound in the aqueous solution gradually increases. The gadolinium compound supersaturated in the aqueous solution is deposited toward the bottom of the container. This time point may be determined as an immersion time of the compound. However, according to the degree of vacuum pumping, the deposition of the gadolinium compound may be performed too fast. In the above, the sample and the aqueous solution are heated together, which is for an action of enhancing the penetration rate of the aqueous solution into the rock sample and for preventing the gadolinium compound from being deposited too fast.

In this embodiment, the above function is implemented by alternately and repeatedly performing the process of loading a container in an oven while the vacuum pumping is performed and heating the container.

As described above, when the deposition of the gadolinium compound in the pores is completed, the second image is then captured. Before the second image is captured, the above-mentioned preprocessing processes may be performed in the same way. A process of flattening, grinding, coating with a metal having high electrical conductivity, and the like are performed, and thus, a cross-section of the rock sample is formed to capture an SEM image. Subsequently, the second image is captured by using an SEM. As described above, the second image may also be captured by selecting a plurality of regions in the cross-section of the rock sample, and capturing conditions with respect to the plurality of regions are favorably set so as to be maximally the same. This is the same as the description on the first image, and will thereby be omitted.

When the second image is obtained, the area (second area) of portions appearing brighter than a predetermined level on the SEM image is calculated. The portions appearing bright are the portions of pores in which the gadolinium compound is deposited and heavy minerals (including portions bonded to the surface of the gadolinium compound). The second area may express, using a percent ratio, the portions occupied in the entire second image.

Since the portions of the pores are added, the area (the second area) of the bright portions in the second image will appear, of course, wider than the area (the first area) of the bright portions on the first image. Accordingly, when the first area is subtracted from the second area, the pure area of the pores may be calculated. In addition, since a plurality of regions are imaged in the cross-section of the imaged rock sample, an error rate of the porosity may be reduced by averaging the areas of the regions.

Hereinafter, processing of the SEM image will be described in more detail.

Figure 2:
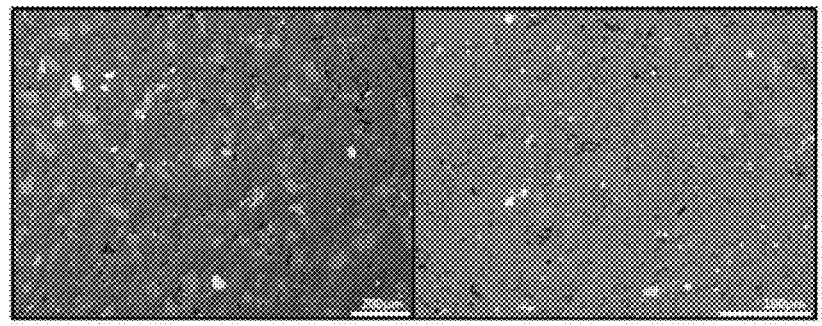
FIG. 2 shows photographs of a BSE image of an SEM captured from a dense stratum (left view) and shale (right view).

A BSE image is mainly used as the SEM image, and an SE image is used as an auxiliary data for observing other features. As illustrated in FIG. 2, in the BSE image, in the case of materials having substantially low density states or low-density materials such as pores or organics, the image pixels corresponding thereto exhibit very low graylevel values and are mainly expressed as black-based colors. As illustrated in FIG. 2, in general, pores in the rock have small sizes and are often associated with portions having relatively low density in the rock media. Accordingly, on the BSE image prior to gadolinium processing, the rock media and the pores are not so easily discriminated by using the graylevels of the image pixels. In particular, when the pores are present at borders of the rock media particles or the resolution of the corresponding image reaches a limit because the sizes of the pores are very small, the above discrimination becomes more difficult.

Meanwhile, as illustrated in FIG. 2, in this case, pixels representing heavy metal compounds (or heavy minerals) in the BSE image have a high brightness range which is clearly discriminated than the pixels corresponding to other rock media, that is, have a very high graylevel range.

Figure 3:
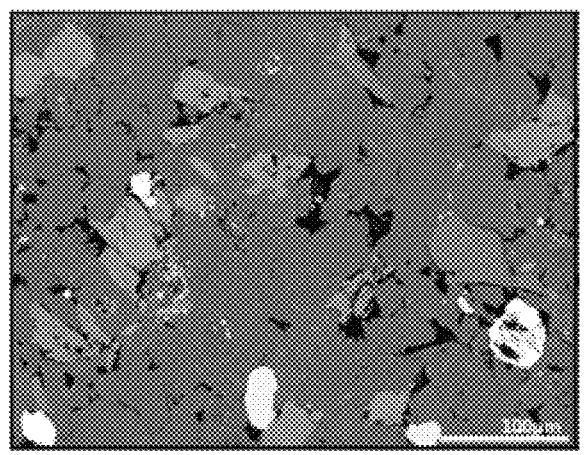
FIG. 3 is a view illustrating an SEM image of a rock in a dense stratum prior to a reaction with a gadolinium compound and contents of heavy metal compounds (or heavy minerals) (white/light colored high brightness areas) in the rock are quantitatively calculated from the SEM image, according to a preferred exemplary embodiment of the present invention.

Accordingly, as illustrated in FIG. 3, in this BSE image of an SEM, when the high graylevel range of the heavy metals compounds (or heavy minerals) is used, the heavy metal compound (or heavy minerals) may be relatively easily separated and discriminated even in a non-conventional reservoir such as a dense stratum, and thus, the content thereof may be more accurately calculated.

Figure 4:
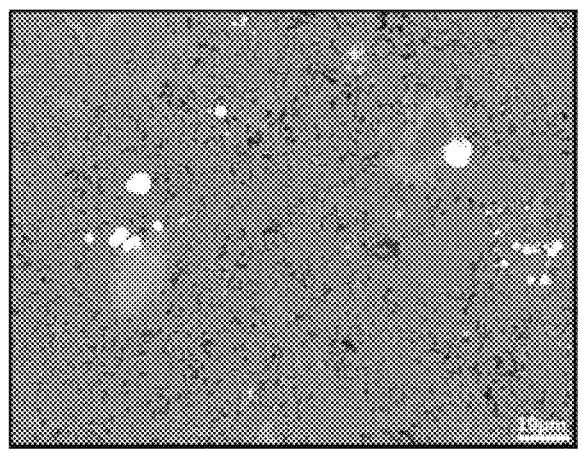
FIG. 4 is a view illustrating an SEM image of a shale rock prior to a reaction with a gadolinium compound and contents of heavy metal compounds (or heavy minerals) (white/light colored high brightness areas) in the rock are quantitatively calculated from the SEM image, according to a preferred exemplary embodiment of the present invention.

Also, as illustrated in FIG. 4, in this BSE image of an SEM, when the high graylevel range of the heavy metal compounds (or heavy minerals) is used, the heavy metal compounds (or heavy minerals) may be relatively easily separated and discriminated even in a non-conventional reservoir such as shale, and thus, the content thereof may be more accurately calculated.

Figure 5:
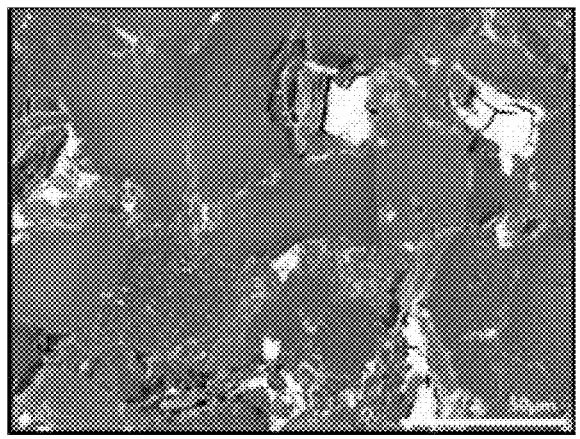
FIG. 5 is a view illustrating: a total content (white/light colored high brightness areas) of heavy metal compounds (or heavy minerals) originally distributed in a rock and a gadolinium compound, which newly penetrates into and is deposited in the rock, is calculated from an SEM image of the rock in a dense stratum after a reaction with a gadolinium compound; cracking pores (black/dark colored low brightness areas) newly generated in places in which the gadolinium compound penetrates; and a sum of the heavy metal compound areas and the cracking pore areas are quantified, according to a preferred exemplary embodiment of the present invention.

As illustrated in FIG. 5, in the BSE image of an SEM after the gadolinium processing, by virtue of the gadolinium compound penetrating into pores, the image pixels corresponding to original pores in the rock exhibit a high brightness range more clearly discriminated than image pixels corresponding to media of other rock media which penetrate and are deposited in the pores, and as illustrated in FIG. 5, appear in white-based colors similar to the graylevels of other heavy metal compounds (or heavy minerals). Accordingly, as illustrated FIG. 5, when the BSE image after the gadolinium processing is used, by virtue of the high graylevel range of the gadolinium compound penetrating into pores, linear pores which have very small widths and are distributed between constituent particles of rocks in a non-conventional reservoir such as dense strata, or a very small pores close to the resolution limit of the corresponding image may be easily found.

One more important meaning illustrated by FIG. 5 is that when the aqueous solution of the gadolinium compound is reacted with the rock as in the present invention, the aqueous solution penetrates into and is successfully deposited in the pores up to those having widths or sizes of nanometer level which is close to the resolution limit of the SEM. Thus, it may be determined that the BSE image of the rock after the gadolinium processing faithfully reflects all pores in which oil and gas are stored in the rock.

In addition, as illustrated FIG. 5, in the process of drying the rock sample after the gadolinium processing, cracks sometimes occur in the deposited gadolinium portion and may also be observed as pores. These cracks due to an experiment may be minimized in the process of allowing the gadolinium aqueous solution to penetrate the rock, by properly adjusting the concentration of the gadolinium aqueous solution according to the rock media characteristics such that a maximal amount of deposition occurs.

In addition, as illustrated in FIG. 5, even when cracks occur in portions, in which gadolinium penetrates, and change into pores, only the pore portions contacting the deposited gadolinium compound may sufficiently be separately separated and discriminated by some of the methods of the present invention. Accordingly, as illustrated in FIG. 5, the pores separately separated and discriminated as such, and the original portion in which gadolinium compound is deposited, are added and quantified, and thus, a calculation error may maximally be prevented.

Figure 6:
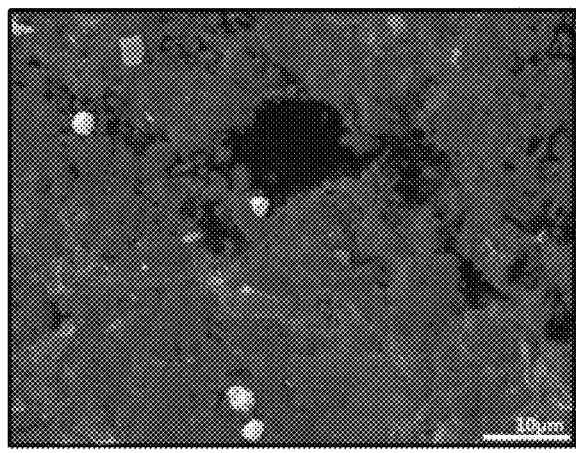
FIG. 6 is a view illustrating an example in which from an SEM image of a shale rock after a reaction with a gadolinium compound, heavy metal compounds (or heavy minerals) originally distributed in a rock and a gadolinium compound, which newly penetrates into and is deposited in the rock, are quantified together (white/light colored high brightness areas), according to a preferred exemplary embodiment of the present invention.

Meanwhile, as illustrated in FIG. 6, in a BSE image after the gadolinium processing with respect to a shale sample, the gadolinium compound penetrates and deposited even into pores having more fine scale than a dense stratum, so that the image pixels of the portions appear in a high graylevel range which is more clearly discriminated than the image pixels of other rock media, that is, appear in a higher brightness range similar to other heavy metal compounds (or heavy minerals), that is, in white-based colors.

As illustrated in FIG. 6, due to the characteristics of a proper processing of the gadolinium compound or the pores of an original rock, unless new cracks occur between the gadolinium deposited portions even during a sample drying process, the process of additionally calculating the newly occurring cracks such as those illustrated in the center and the right side of FIG. 5 are not necessarily performed and may be omitted.

As illustrated in FIGS. 5 and 6, when the high graylevel range appearing in the image pixels of the BSE image of the SEM with respect to the rock sample after gadolinium compound processing is used, the total content of heavy metal compounds (or heavy minerals) in the rock and the gadolinium compound may be quantified.

Sometimes, the gadolinium compound deposited in pores of the rock may exhibit a graylevel range which is consistently discriminated from that of other heavy metal compounds (or heavy minerals) which are already present in the rock. In this case, the gadolinium compound and other heavy metal compounds (or heavy minerals) may be separately separated and discriminated and quantified by using the graylevel range, but such a case is not so common.

In addition, like the above-mentioned processes, when the contents of heavy metal compounds (or heavy minerals) are calculated from the SEM image prior to the gadolinium compound processing, and when the content of the gadolinium compound, which penetrates into and is deposited in heavy metal compounds (or heavy minerals) and the pores of the rock, are then calculated together, the original porosity of the rock may be calculated by using the calculated values. That is, when a quantified value of only heavy metal compounds (or heavy minerals) is subtracted from a simultaneously quantified value of heavy metal compounds and the gadolinium compound, the original porosity of the rock may be calculated.

Figure 7:
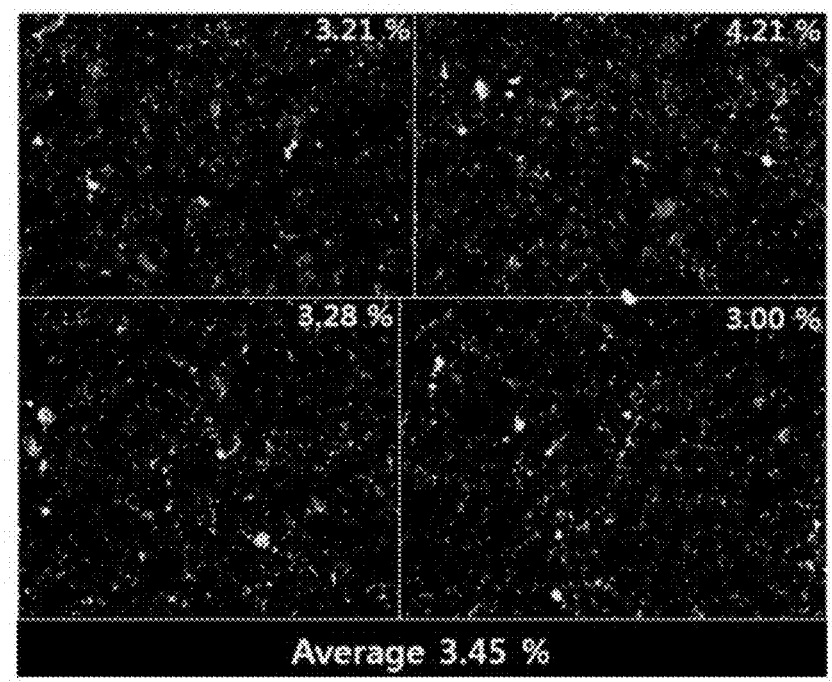
FIG. 7 is a view illustrating an example, in which calculated values which are obtained not from one SEM image but from a plurality of SEM images, are averaged to thereby calculate a more reliable calculated value, according to a preferred exemplary embodiment of the present invention.

As illustrated in FIG. 7, to enhance the reliability of the calculation of the porosity, a plurality of SEM images captured from the rock sample before and after the gadolinium processing may be used for the calculation. That is, an average value of the contents of the heavy metal compounds (or heavy minerals) is calculated from the plurality of SEM images captured from the rock sample before the gadolinium processing, and the total content of the gadolinium compound, which penetrates into and is deposited in heavy metal compounds (or heavy minerals) and the pores of the rock is calculated as an average value. Then, when porosity is calculated by using the two average values, more reliable porosity may be obtained.

So far, preferred exemplary embodiments of the present invention have been described with reference to some examples, but the above descriptions are provided merely as examples. Any one skilled in the art belonging to the present invention would well understand that from the description above, the present invention can be implemented in a form in which various changes and modifications are made, or in a form equivalent to the present invention.

What is claimed is:

1. A method for measuring porosity of a rock sample comprising:
    capturing a first Scanning Electron Microscope (SEM) image of the rock sample;
    determining a first heavy metal area percentage of the first SEM image;
    filling pores of the rock sample with an aqueous solution comprising a gadolinium compound;
    capturing a second SEM image of the rock sample filled with the aqueous solution comprising the gadolinium compound;
    determining a second heavy metal area percentage and a pore area percentage of the second SEM image; and
    calculating the porosity of the rock sample by calculating a sum of the second heavy metal area percentage and the pore area percentage of the second SEM image, and subtracting the first heavy metal area percentage of the first SEM image from the sum.

2. The method of claim 1, wherein the first heavy metal area percentage and the second heavy metal area percentage are determined by using graylevels on an image.

3. The method of claim 1, wherein the gadolinium compound is gadolinium nitrate ($GdN_3O_9 \cdot 5(H_2O)$).

4. The method of claim 1, further comprises preprocessing the rock sample by grinding a surface of the rock sample.

5. The method of claim 4, wherein the preprocessing further comprises coating the surface of the rock sample with a material having high electrical conductivity including gold or platinum.

6. The method of claim 1, wherein a concentration of the gadolinium compound in the aqueous solution allows the gadolinium compound to penetrate into the pores of the rock sample.

7. The method of claim 1, wherein filling pores of the rock sample with the aqueous solution comprises immersing the rock sample in the aqueous solution, and wherein the aqueous solution is heated to improve a penetration rate of the gadolinium compound into the rock sample.

8. The method of claim 1, wherein filling pores of the rock sample with the aqueous solution comprises immersing the rock sample in the aqueous solution in a vacuum chamber.

9. The method of claim 1, wherein filling pores of the rock sample with the aqueous solution comprises immersing the rock sample in the aqueous solution until the aqueous solution fills the pores of the rock sample.

10. The method of claim 1, wherein capturing the first SEM image and capturing the second SEM image comprising capturing the first SEM image and the second SEM image of a same rock sample.

11. The method of claim 1, wherein capturing the first SEM image comprises capturing the first SEM image of a first rock sample from a rock, and capturing the second SEM image comprises capturing the second SEM image from a second rock sample from the rock.

* * * * *